US00PP26332P3

(12) United States Plant Patent
Ui et al.

(10) Patent No.: US PP26,332 P3
(45) Date of Patent: Jan. 19, 2016

(54) PETUNIA-CALIBRACHOA HYBRID PLANT NAMED 'SAKPXC012'

(50) Latin Name: ***Petunia-Calibrachoa* intergeneric hybrid**
Varietal Denomination: SAKPXC012

(71) Applicant: Sakata Seed Corporation, Yokohama (JP)

(72) Inventors: Akinobu Ui, Iwata (JP); Shin Ishikawa, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 153 days.

(21) Appl. No.: 13/999,831

(22) Filed: Mar. 26, 2014

(65) Prior Publication Data

US 2015/0282410 P1 Oct. 1, 2015

(51) Int. Cl.
*A01H 5/00* (2006.01)

(52) U.S. Cl.
USPC ..... Plt./356.11

(58) Field of Classification Search
USPC ..... Plt./356.11
See application file for complete search history.

(56) References Cited

PUBLICATIONS

PLUTO Plant Variety Database Jul. 22, 2015. p. 1.*

* cited by examiner

*Primary Examiner* — Annette Para
(74) *Attorney, Agent, or Firm* — Barbara Campbell; Bethany Reid Roahrig; Cochran Freund & Young LLC

(57) ABSTRACT

A new *Petunia-Calibrachoa* hybrid plant particularly distinguished by having a cherry rose flower color and semi-creeping plant growth habit, is disclosed.

1 Drawing Sheet

Genus and species: *Petunia-Calibrachoa* intergeneric hybrid.

Variety denomination: 'SAKPXC012'.

BACKGROUND OF THE NEW PLANT

The present invention comprises a new and distinct variety of *Petunia-Calibrachoa* (Petchoa) referred to by the variety name 'SAKPXC012'. Variety 'SAKPXC012' originated from a hybridization in Kakegawa, Japan in December 2007. The male parent was a proprietary hybrid *calibrachoa* line named 'CBR-1' (unpatented), which has a red flower color and a creeping plant habit. The female parent is a proprietary hybrid petunia line named 'AM5-264' (unpatented), which has a deep pink flower color and a mounding plant habit.

In December 2007, an $F_1$ generation from the initial hybridization was grown and approximately 30 seeds were obtained. In February 2008, 30 seeds were sown and the plants were cultivated in a greenhouse. Segregation in the $F_1$ generation resulted in plants having a rose and cherry rose flower color and a mounding and semi-creeping plant habits. In May 2008, a plant was selected from the group of plants that exhibited a cherry rose flower color and semi-creeping plant habit. The line was given the experimental name 'K2008-J-229'.

In July 2008, the selection was vegetatively propagated to produce rooted cuttings, and the plants were cultivated in an open field. In November 2008, the selection was observed to have its distinct characteristics remain stable. In February 2009, the selection was propagated again and plants were cultivated. In May 2009, it was confirmed that the distinct characteristics of the selection were fixed and stable. The selection was given the experimental name 'K2008-J-229'. The selection was later named 'SAKPXC012' and was found to reproduce true to type in successive generations of asexual propagation via vegetative cuttings in Salinas, Calif.

SUMMARY

The following are the most outstanding and distinguishing characteristics of this new variety when grown under normal horticultural practices in Salinas, Calif.

1. Cherry rose flower color; and
2. A semi-creeping plant habit.

DESCRIPTION OF THE PHOTOGRAPHS

This new *Petunia-Calibrachoa* plant is illustrated by the accompanying photographs which show the plant's overall plant habit including form, foliage, and flowers. The photographs are of a four-month-old plant grown in Salinas, Calif. under greenhouse conditions in Fall 2013. The colors shown are as true as can be reasonably obtained by conventional photographic procedures.

DESCRIPTION OF THE NEW VARIETY

Figure 1:
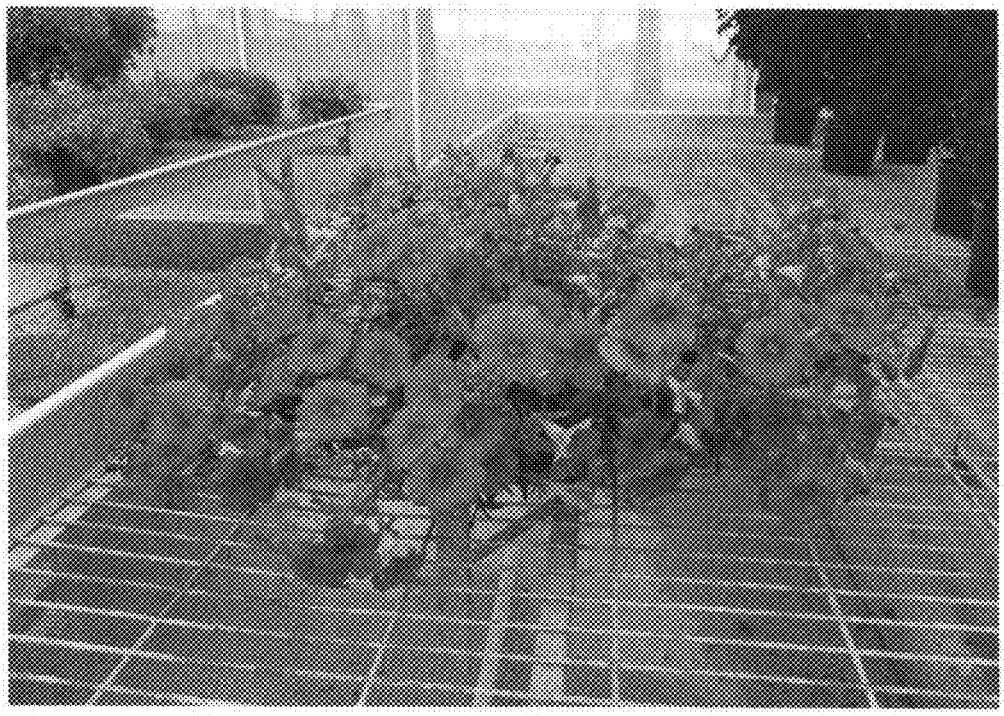
FIG. 1 shows the overall plant habit of the plant grown in a pot.
Figure 2:
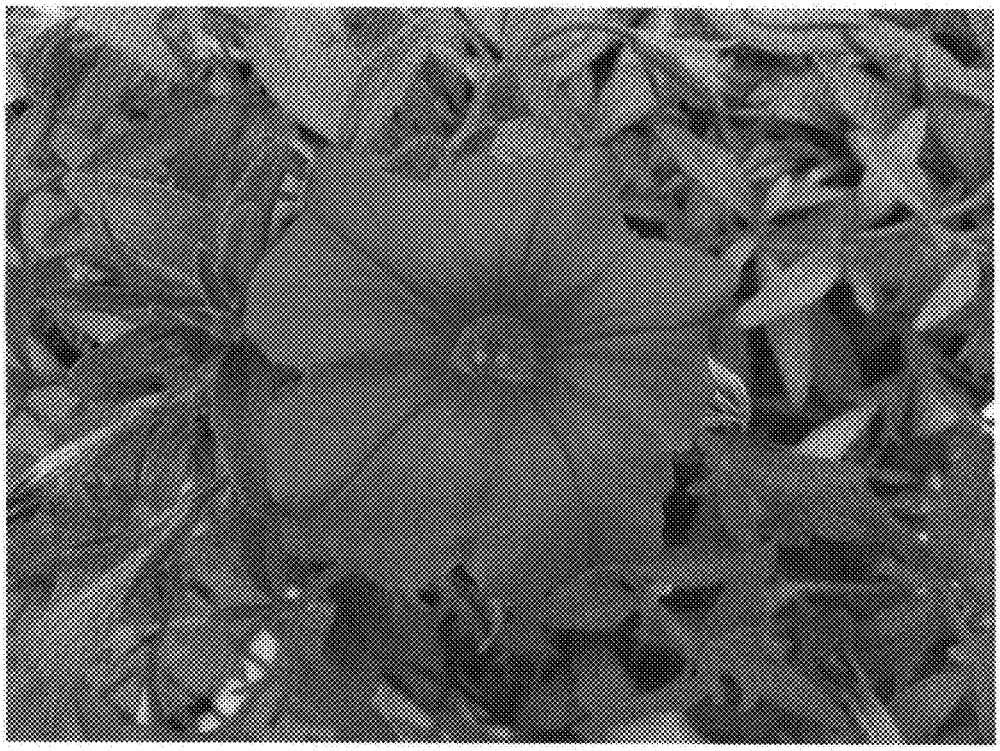
FIG. 2 shows a close-up of the foliage and flower.

The following detailed descriptions set forth the distinctive characteristics of 'SAKPXC012'. The data which define these characteristics were collected from asexual reproductions carried out in Salinas, Calif. Data was collected on four-month-old plants grown under greenhouse conditions in Salinas, Calif. in the spring of 2014. Color references are to The R.H.S. Colour Chart of The Royal Horticultural Society of London (R.H.S.), $4^{th}$ edition. Anatomic labels are from *The*

*Cambridge Illustrated Glossary of Botanical Terms*, by M. Hickey and C. King, Cambridge University.

Classification:

*Family*.—Solanaceae.

*Botanical*.—*Petunia-Calibrachoa* hybrid.

*Common*.—Petchoa, *petunia-calibrachoa*.

*Designation*.—'SAKPXC012'.

Parentage:

*Female parent*.—Proprietary hybrid *petunia* plant line 'AM5-264' (unpatented).

*Male parent*.—Proprietary hybrid *calibrachoa* plant line 'CBR-1' (unpatented).

Growth:

*Time to produce a rooted cutting*.—4 weeks.

*Time to bloom from propagation*.—8 to 10 weeks.

*Environmental conditions for plant growth*.—The terminal 1.0 to 1.5 inches of an actively growing stem was excised. The vegetative cuttings were propagated in five to six weeks. The base of the cuttings were dipped for 1 to 2 seconds in a 1:9 solution of DIP 'N GROW (1 solution: 9 water), a root inducing solution, immediately prior to sticking into the cell trays. Cuttings were stuck into plastic cell trays having 98 cells, and containing a moistened peat moss-based growing medium. For the first week, the cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Plant description:

*Habit*.—Semi-creeping.

*Life cycle*.—Tender perennial.

*Height* (*from soil line to top of foliage*).—15.0 cm.

*Spread*.—45.0 cm.

Stems:

*General*.—Dull in appearance and circular in cross-section.

*Stem length*.—1.0 cm from soil line to first node; 22.0 cm in length from end to end.

*Diameter*.—0.3 cm.

*Internode length*.—1.5 cm.

*Color*.—RHS 144A (Yellow-Green).

*Pubescence*.—Heavy, color is RHS N155A (White).

*Anthocyanin color*.—Absent.

Leaves:

*Arrangement*.—Alternate.

*Shape*.—Elliptic.

*Apex*.—Obtuse.

*Base*.—Attenuate.

*Margin*.—Entire.

*Venation*.—Pinnate.

*Surface appearance* (*both surfaces*).—Dull.

*Surface pubescence* (*both surfaces*).—Light; pubescence is RHS N155A (White).

*Length*.—5.5 cm.

*Width*.—1.7 cm.

*Color*.—Upper surface: RHS 137A (Yellow-Green). Lower surface: RHS 138B (Yellow-Green).

*Fragrance*.—Absent.

*Petiole*.—Absent.

Flowers:

*Total number of flowers* (*per plant*).—Approximately 77.

*Flowering habit*.—Indeterminate.

*Flower type*.—Solitary.

*Flowering requirements*.—Will flower so long as day length is greater than 12 hours and temperature exceeds 13° C.

*Duration of flowers*.—5 days.

*Shape*.—The flowers are funnel shaped with five fissures and a shallow, yet slight, indentation of the petal tip at the midvein.

*Fragrance*.—Absent.

Flower buds:

*Surface texture*.—Pubescent.

*Length*.—3.1 cm.

*Diameter*.—1.4 cm.

*Shape*.—Ovate.

*Color*.—RHS N79C (Purple) with RHS N79A (Purple) veins.

Peduncle:

*Length*.—1.9 cm.

*Diameter*.—0.1 cm.

*Color*.—RHS 144B (Yellow-Green) with some anthocyanin, which is RHS N187A (Greyed-Purple).

*Texture*.—Dull, light pubescence, pubescence color is RHS N155A (White).

Flower description:

*Flower depth*.—1.0 cm.

*Flower diameter*.—4.2 cm.

*Flower tube length*.—2.5 cm.

*Flower tube diameter*.—0.5 cm.

Calyx:

*Arrangement*.—Composed of 5 sepals, fused below the middle.

*Sepals*.—Shape: Elliptic. Apex: Obtuse. Margin: Entire. Length: 2.5 cm. Diameter: 5.0 mm. Color (both surfaces): RHS 137C (Green).

Corolla:

*Arrangement*.—Composed of 5 petals, fused.

*Diameter*.—5.0 cm.

*Petal*.—Apex: Truncate. Margin: Entire. Base: Fused. Pubescence (both surfaces): Glabrous. Lobe length: 3.0 cm. Lobe width: 2.3 cm. Color: Upper surface: Closest to but brighter than RHS 61B (Red-Purple). Lower surface: RHS 63C (Red-Purple).

*Corolla tube color*.—Inner: Closest to RHS 13A (Yellow). Outer: RHS 10A (Yellow) with RHS 143A (Green) veins.

Reproductive organs:

*Stamen number*.—5, free.

*Stamen length*.—1.0 cm.

*Anther color*.—3A (Yellow).

*Stamen color*.—RHS 150D (Yellow-Green).

*Filament color*.—RHS 11C (Yellow).

*Pollen color*.—RHS 3B (Yellow).

*Pollen amount*.—Abundant.

*Ovary*.—Superior.

*Placenta arrangement*.—Central.

*Pistil number*.—1 per inflorescence.

*Pistil length*.—1.7 cm.

*Stigma color*.—RHS 141B (Yellow-Green).

*Style length*.—1.5 cm.

*Style color*.—RHS 149C (Yellow-Green).

Seed production: None observed.

Disease and insect resistance: Excellent resistance to rain, heat and drought. Will not tolerate temperatures below 10° C. Plants are susceptible to *Botrytis,* powdery mildew, various stem and root rots, and certain viruses, like Tobacco Mosaic Virus and Impatiens Necrotic Spotted Virus. Plants can be infested with aphids, leafminer, whitefly and various Lepitopdera.

COMPARISON WITH PARENTAL LINES AND KNOWN VARIETY

'SAKPXC012' is a new and unique variety of intergeneric *Petunia-Calibrachoa* owing to its cherry rose flower color and semi-creeping plant growth habit. 'SAKPXC012' is distinguished from its parents mainly by flower color and plant growth habit as shown in Table 1 below):

TABLE 1

| Characteristic | 'SAKPXC012' | Male Parent 'CBR-1' | Female Parent 'AM5-264' |
|---|---|---|---|
| Flower color | Cherry rose | Red | Deep pink |
| Plant growth habit | Semi-creeping | Creeping | Mounding |

'SAKPXC012' is a new and unique variety of intergeneric *Petunia-Calibrachoa* owing to its rose flower color and semi-creeping plant growth habit. 'SAKPXC012' is most similar to the commercial *Petunia-Calibrachoa* variety 'SAKPXC007' (U.S. Plant Pat. No. 21,853), commercially known as Super-Cal® 'Cherry'; however there are differences in the flower color as described in the table below (color references are to The Royal Horticultural Society Colour Chart, 4th edition) and growth habit as shown in Table 2:

TABLE 2

| Characteristic | 'SAKPXC012' | 'SAKPXC007' |
|---|---|---|
| Petal color, upper surface | Closest to but brighter than RHS 61B (Red-Purple) | Closest to RHS 61B |
| Petal color, lower surface | RHS 63C (Red-Purple) | RHS 59D (Red-Purple) with RHS N77A (Purple) veins |
| Plant growth habit | Semi-creeping | Mounding |

We claim:

1. A new and distinct cultivar of *Petunia-Calibrachoa* hybrid plant as shown and described herein.

* * * * *